(12) United States Patent
Zhou (10) Patent No.: US 10,376,664 B2
(45) Date of Patent: Aug. 13, 2019

(54) ARTIFICIAL AIRWAY SPUTUM SCAB CLEANER

(71) Applicant: Sanlian Zhou, Jiangsu (CN)

(72) Inventor: Sanlian Zhou, Jiangsu (CN)

( * ) Notice: Subject to any disclaimer, the term of this patent is extended or adjusted under 35 U.S.C. 154(b) by 0 days.

(21) Appl. No.: 16/022,635

(22) Filed: Jun. 28, 2018

(65) Prior Publication Data

US 2019/0015616 A1 Jan. 17, 2019

(30) Foreign Application Priority Data

Jul. 13, 2017 (CN) .......................... 2017 1 0570781

(51) Int. Cl.
| | |
|---|---|
| *A61M 16/04* | (2006.01) |
| *A61M 1/00* | (2006.01) |
| *A61B 1/267* | (2006.01) |
| *A61B 1/015* | (2006.01) |
| *A61B 1/00* | (2006.01) |

(52) U.S. Cl.
CPC ......... *A61M 16/0463* (2013.01); *A61B 1/015* (2013.01); *A61M 16/0477* (2014.02); *A61B 1/00087* (2013.01); *A61B 1/00094* (2013.01); *A61M 1/0025* (2014.02); *A61M 2205/502* (2013.01); *A61M 2209/10* (2013.01)

(58) Field of Classification Search
CPC ........... A61B 1/00052; A61B 1/00068; A61B 1/00087; A61B 1/00094; A61B 1/015; A61B 1/267; A61B 16/0463; A61B 16/0402; A61B 16/0477; A61B 2017/00246; A61M 1/0025; A61M 2209/10; A61M 2205/502
See application file for complete search history.

(56) References Cited

U.S. PATENT DOCUMENTS

| | | | | |
|---|---|---|---|---|
| 2006/0264988 A1* | 11/2006 | Boyle | ................... | A61M 27/00 606/159 |
| 2008/0248673 A1* | 10/2008 | Boehnlein | .......... | A61B 1/00052 439/320 |
| 2009/0149716 A1* | 6/2009 | Diao | ................... | A61B 1/00085 600/202 |
| 2013/0104884 A1* | 5/2013 | Vazales | .................. | A61B 1/267 128/202.16 |
| 2014/0150782 A1* | 6/2014 | Vazales | ............. | A61M 16/0463 128/202.16 |
| 2014/0288371 A1* | 9/2014 | Nakatate | ................. | A61B 1/267 600/156 |
| 2015/0343182 A1* | 12/2015 | Vazales | .................. | A61B 1/122 604/267 |
| 2018/0193050 A1* | 7/2018 | Hawkins | ............ | A61B 1/00085 |

FOREIGN PATENT DOCUMENTS

| | | | |
|---|---|---|---|
| CN | 204411452 U | * | 6/2015 |
| CN | 105709282 A | * | 6/2016 |

\* cited by examiner

*Primary Examiner* — John P Leubecker (74) *Attorney, Agent, or Firm* — Wayne & Ken, LLC; Tony Hom (57) ABSTRACT

An artificial airway sputum scab cleaner including a connection hub, a display window, a detection tube, a sputum suction tube, a sputum suction device, a probe head a hooking device, a light beam device and a camera device; the hooking device includes a hooking channel, a hooking spoon, a push rod and a permanent magnet, an iron sheet, a first coil.

9 Claims, 5 Drawing Sheets

FIG. 5

ARTIFICIAL AIRWAY SPUTUM SCAB CLEANER

TECHNICAL FIELD

The present invention relates to the technical field of medical equipment, and more particularly, to an artificial airway sputum scab cleaner.

BACKGROUND

At present, patients with tracheal intubation or tracheotomy cannot spit spontaneously. When patients have sputum, it is often necessary to suck the sputum out. It is also necessary to suck sputum from patients with lung infection when they have weak expectoration. Sputum suction tubes are commonly used when sucking sputum, which can suck sputum out of the body and solve the problem that patients may have sputum suffocation. However, it is necessary to find a specific location for sputum suction before suction is performed. Since the suction location is not visible, the sputum suction tube cannot accurately suck the sputum, which leads to the formation of sputum scabs. Prolonged stay of sputum scabs in the patients will bring great pain to the patients, wasting a lot of treatment time and even causing the patients to lose their lives.

Moreover, in the current circuit application of electronic medical instruments, the problem of switching between external signals and internal signals is often encountered, that is, when an external signal is input, the circuit automatically switches to the external signal; while when the signal is removed, the circuit automatically returns to an internal signal input state. A typical technical case is the switching between an internal MIC and an external MIC.

At present, there are several solutions for signal switching:

First, the switching is performed by a mechanical switching structure or is performed manually. However, both of these methods will lead to a limited service life of the mechanism and a low switching speed. Moreover, unnecessary noise interference will be introduced into the switching mechanism, which cannot be digitally controlled, and the contacts will easily oxidize.

Secondly, a relay is used for switching. The relay acts as a single-pole double-throw switch to switch the internal and external signals, which solves the problem of digital control. However, the volume of the circuit increases, the switching speed is not fast, and the contacts are also easy to oxidize.

Thirdly, an analog switch is used for switching, which acts as a single-pole and double-throw switch. However, the typical analog switch CD4053 has a minimum on-resistance of about 80 ohms. The on-resistance of the high-end analog switch MAX4887 is also about 5 ohms. The on-resistance is relatively large, which will seriously affect the communication distance when the analog switch is used on the communication line.

To sum up, there is an urgent need for a conversion circuit which has small resistance, high efficiency, stability and small interference, so as to improve the overall signal conversion quality and reduce the response time of electronic medical instruments, thereby improving the efficiency.

In view of the problems in the related art, no effective solution has been put forward by now.

SUMMARY

In view of the problems in the related art, the present invention provides an artificial airway sputum scab cleaner to overcome the above technical problems existing in the prior art.

The technical solution of the invention is implemented as follows.

An artificial airway sputum scab cleaner comprises a connection hub, wherein a display window is arranged in a side face of the connection hub; a detection tube is arranged on a side face of the connection hub opposite to the display window; a sputum suction tube is inserted through the detection tube; a sputum suction device is arranged on a bottom face of the connection hub; a probe head is arranged at one end of the detection tube away from the connection hub; a hooking device, a light beam device and a camera device are arranged at the periphery of the sputum suction tube; the hooking device comprises a hooking channel, a hooking spoon, a push rod and a permanent magnet; the hooking channel is arranged in the probe head; the hooking spoon, the push rod and the permanent magnet are respectively arranged in the hooking channel; the hooking spoon is connected with the push rod; the push rod is connected with the permanent magnet; iron sheets are arranged on a side face of the push rod; a first coil is arranged at one end of the hooking channel close to the permanent magnet; a plurality of second coils are equidistantly arranged at a side face of one end of the hooking channel away from the permanent magnet; the light beam device comprises a light beam groove and a light beam lamp; the light beam groove is positioned on the surface of the probe head, and the light beam lamp is fixed inside the light beam groove; the camera device comprises a camera groove and a camera head; the camera groove is positioned on the surface of the probe head; the camera head is fixed inside the camera groove; a top face of the connection hub is provided with a power supply and a control button; the first coil, the second coils, the light beam lamp and the camera head are respectively connected with the control button through the connection hub; the control button is connected with the power supply; the camera head is connected with the display window through the connection hub; the sputum suction device comprises a suction tube, a lateral valve cylinder, a longitudinal valve cylinder, a pull rod cylinder, a handle and a pull rod; one end of the suction tube is connected with the sputum suction tube through the connection hub, and the other end of the sputum suction tube is connected with the lateral valve cylinder; the pull rod cylinder is connected with the lateral valve cylinder; the handle is fixed on the pull rod cylinder; the pull rod is positioned inside the handle and connected with the pull rod cylinder by passing through the handle; the longitudinal valve cylinder is fixed at the bottom of a side face of the lateral valve cylinder; and a bottom end of the longitudinal valve cylinder is provided with a sputum collecting tank.

In some embodiment, one end of the sputum suction tube away from the connection hub is provided with a ball-shaped suction head.

In some embodiments, the hooking channel is internally provided with a limiting circular plate.

In some embodiments, the number of the camera devices 8 is 2 to 3.

In some embodiments, the number of the light beam devices 7 is 2 to 3.

In some embodiments, the number of the hooking devices 6 is 2 to 4.

In some embodiments, the connection hub 1 is internally provided with a tube adapting interface and a video processor.

In one embodiment, the connection hub 1 further comprises a signal conversion unit which comprises a first operational amplifier, a second operational amplifier, a third operational amplifier, a fourth operational amplifier, a first resistor, a second resistor, a third resistor, a fourth resistor, a fifth resistor, a sixth resistor, a seventh resistor, an eighth resistor, a ninth resistor, a tenth resistor, an eleventh resistor, a first transistor, a first diode, a second diode, a first capacitor, a second capacitor, a third capacitor, a fourth capacitor, a fifth capacitor, a first power supply and a reference power supply, a comparator UI, a first light control relay, and a second light control relay;

positive input terminals of the first operational amplifier and the second operational amplifier receive input signals respectively, negative input terminals of the first operational amplifier and the second operational amplifier are respectively connected with respective output terminals, an input terminal of a relay in the first optical control relay is connected with an output terminal of the first operational amplifier, an input terminal of a relay in the second optical control relay is connected with an output terminal of the second operational amplifier, an output terminal of the relay in the first optical control relay is connected with one end of the second resistor, an output terminal of the relay in the second optical control relay is connected with one end of the third resistor, the other end of the second resistor is connected with the other end of the third resistor, a cathode of the first diode in the first light control relay is grounded, an anode of the first diode in the first light control relay is connected with one end of the first resistor, the other end of the first resistor is connected with a collector of the first transistor, an emitter of the first transistor is connected with the first power supply, a base of the first transistor is connected with one end of the ninth resistor and one end of the first capacitor respectively, the other end of the ninth resistor and the other end of the first capacitor are respectively connected with one end of the fourth resistor, the other end of the fourth resistor is connected with an anode of the second diode in the second light control relay, a cathode of the second diode in the second optical control relay is grounded, the output terminal of the first operational amplifier is also connected with one end of the fifth resistor, and the other end of the fifth resistor is connected with one end of the sixth resistor and one end of the second capacitor, the other end of the second capacitor is connected with the eighth resistor, a positive input terminal of the fourth operational amplifier and an output terminal of the third operational amplifier respectively, the other end of the eighth resistor is connected with the seventh resistor and a negative input terminal of the third operational amplifier respectively, the other end of the seventh resistor is grounded, a positive input terminal of the third operational amplifier is connected with the other end of the sixth resistor and one end of the third capacitor respectively, the other end of the third capacitor is grounded, a negative input terminal of the fourth operational amplifier is connected with the reference power supply, and an output terminal of the fourth operational amplifier is connected with one end of the fifth capacitor, one end of the first capacitor, the other end of the ninth resistor and one end of the fourth resistor, respectively;

the comparator UI includes a pin SB, a pin BAL, a pin VCC+, a pin VCC−, a pin IN+, a pin IN−, a pin CO and a pin EO, wherein the pin SB connected with one end of the eleventh resistor, and the other end of the eleventh resistor is connected with the pin BAL, the pin VCC+, one end of the fourth capacitor, one end of the tenth resistor, the other end of the fifth capacitor and the pin IN−, the other end of the tenth resistor is connected with the pin VCC− and the pin EO, the other end of the fourth capacitor and the pin CO are grounded, and the pin IN+ is connected with one end of the fifth capacitor and the output terminal of the fourth operational amplifier.

In some embodiments, the first transistor is a PNP transistor.

In some embodiments, the first power supply is 5.0 V, the first resistor has a resistance value of 330 ohms, the second resistor has a resistance value of 4.7 kiloohms, the third resistor has a resistance value of 10 kiloohms, the fourth resistor has a resistance value of 330 ohms, and the reference voltage is 2.5 V.

In some embodiments, both the first diode and the second diode use an IN4148 type diode.

The present invention has the following advantageous effects.

By inserting the probe head into the patient, the power supply powers the control button to make the light beam device and the camera device cooperate. The internal condition of the artificial airway within the patient is presented on the display window by the camera head, and an inspector operates according to the condition observed. In case of presence of sputum scab, the sputum scab is sucked into the sputum collecting tank through the sputum suction device. If there is residue attached to the wall of the airway, the control button can be used to energize the first coil to generate magnetism and eject the hooking spoon, and then the direction of the hooking spoon is adjusted through the attraction of the second coils to the iron sheets. By constantly changing the direction of energization of the first coil, the hooking spoon slides back and forth to facilitate the removal of foreign matters adsorbed on the wall of the airway, which is conducive to further removal of the sputum scab. The whole process is simple to operate with real-time monitoring, and is accurate, fast and safe to clean foreign matters, thus greatly saving the treatment time, saving the work intensity of doctors, and greatly reducing the pains of patients during treatment. The signal conversion unit of the present invention can prevent interferences between other circuit devices in the signal conversion unit and an external working circuit and avoid using analog switches as signal switching elements, thus greatly reducing the on-resistance to a milliohm level. In addition, the signal switching circuit of the present invention has the advantages of high signal switching speed, long service life, stable signal conversion, capability of effectively removing burrs, and capability of increasing the input signal range, thus realizing a conversion circuit with small resistance, high efficiency, stability and small interference, so as to improve the overall signal conversion quality, reduce the response time of electronic medical instruments, and thus improve the efficiency.

BRIEF DESCRIPTION OF THE DRAWINGS

In order to more clearly illustrate the embodiments of the present invention or the technical solutions in the prior art, the drawings that need to be used in the embodiments will be described briefly in the following. Obviously, the drawings in the following description are only some embodiments of the present invention. For those of ordinary skill in the art, other drawings can be obtained from these drawings without creative effort.

In which:

1. connecting hub; 2. display window; 3. detection tube; 4. sputum suction tube; 5. probe head; 6. hooking device; 601. hooking channel; 602. hooking spoon; 603. push rod; 604. permanent magnet; 7. light beam device; 701. light beam groove; 702. light beam lamp; 8. camera device; 801. camera groove; 802. camera; 9. iron sheet; 10. first coil; 11. second coils; 12. power supply; 13. control button; 14. suction tube; 15. laterallateral valve cylinder; 16. longitudinal valve cylinder; 17. pull rod cylinder; 18. handle; 19. pull rod; 20. sputum collecting tank; 21. ball-shaped suction head; 22. limiting circular plate.

DETAILED DESCRIPTION

Hereinafter, the technical solutions of the embodiments will be described in a clearly and fully understandable way in connection with the drawings related to the embodiments of the present invention. Apparently, the described embodiments are just a part but not all of the embodiments of the present invention. Based on the described embodiments herein, those skilled in the art can obtain other embodiment(s) which should be within the scope of the invention.

According to an embodiment of the invention, an artificial airway sputum scab cleaner is provided.

As shown in FIGS. 1-4, the artificial airway sputum scab cleaner according to an embodiment of the invention comprises a connection hub 1. A display window 2 is arranged in a side face of the connection hub 1. A detection tube 3 is arranged on a side face of the connection hub 1 opposite to the display window 2. A sputum suction tube 4 is inserted through the detection tube 3. A sputum suction device is arranged on a bottom face of the connection hub 1. A probe head 5 is arranged at one end of the detection tube 3 away from the connection hub 1. A hooking device 6, a light beam device 7 and a camera device 8 are arranged at the periphery of the sputum suction tube 4. The hooking device 6 comprises a hooking channel 601, a hooking spoon 602, a push rod 603 and a permanent magnet 604. The hooking channel 601 is arranged in the probe head 5. The hooking spoon 602, the push rod 603 and the permanent magnet 604 are respectively arranged in the hooking channel 601. The hooking spoon 602 is connected with the push rod 603 which is connected with the permanent magnet 604. Iron sheets 9 are arranged on a side face of the push rod 603. A first coil 10 is arranged at one end of the hooking channel 601 close to the permanent magnet 604. A plurality of second coils 11 are equidistantly arranged at a side face of one end of the hooking channel 601 away from the permanent magnet 604. The light beam device 7 comprises a light beam groove 701 and a light beam lamp 702. The light beam groove 701 is positioned on the surface of the probe head 5, and the light beam lamp 702 is fixed inside the light beam groove 701. The camera device 8 comprises a camera groove 801 and a camera head 802. The camera groove 801 is positioned on the surface of the probe head 5. The camera head 802 is fixed inside the camera groove 801. A top face of the connection hub 1 is provided with a power supply 12 and a control button 13. The first coil 10, the second coils 11, the light beam lamp 702 and the camera head 802 are connected with the control button 13 through the connection hub 1, respectively. The control button 13 is connected with the power supply 12. The camera head 802 is connected with the display window 2 through the connection hub 1. The sputum suction device comprises a suction tube 14, a lateral valve cylinder 15, a longitudinal valve cylinder 16, a pull rod cylinder 17, a handle 18 and a pull rod 19. One end of the suction tube 14 is connected with the sputum suction tube 4 through the connection hub 1, and the other end of the sputum suction tube 4 is connected with the lateral valve cylinder 15. The pull rod cylinder 17 is connected with the lateral valve cylinder 15. The handle 18 is fixed on the pull rod cylinder 17. The pull rod 19 is positioned inside the handle 18 and connected with the pull rod cylinder 17 by passing through the handle 18. The longitudinal valve cylinder 16 is fixed at the bottom of a side face of the lateral valve cylinder 15. A sputum collecting tank 20 is provided at a bottom end of the longitudinal valve cylinder 16.

Figure 1:
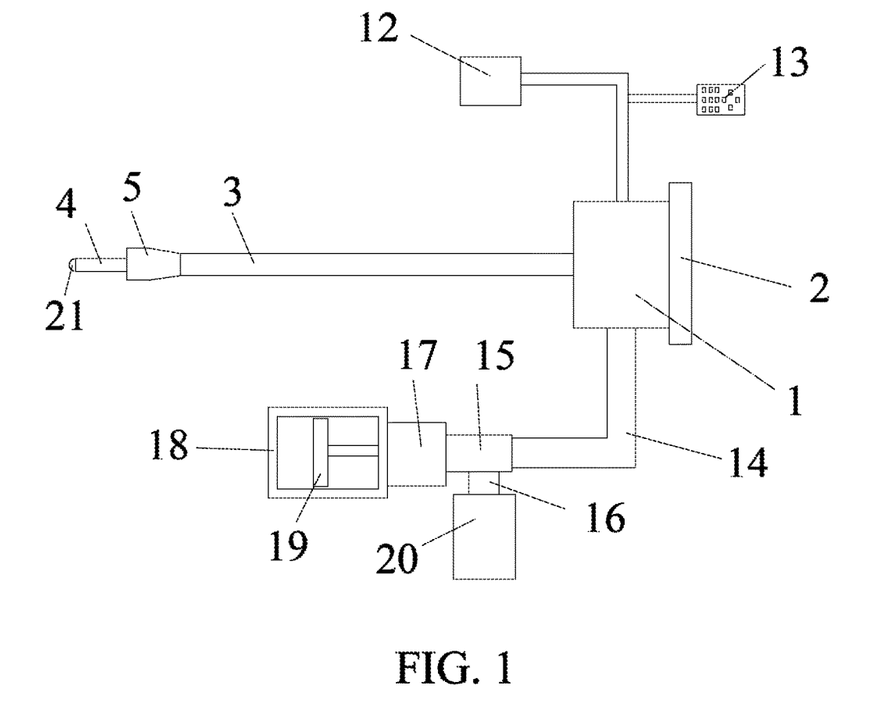
FIG. 1 is a schematic structural view of an artificial airway sputum scab cleaner according to one embodiment of the present invention.
Figure 2:
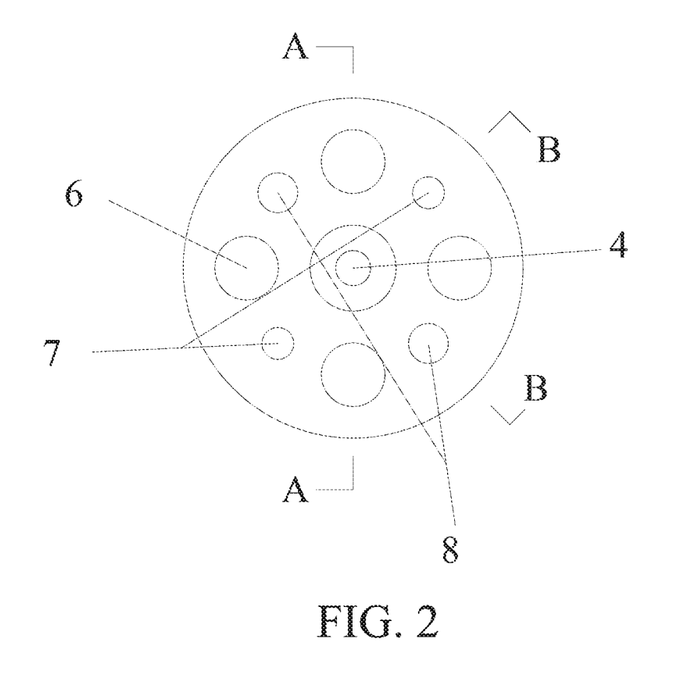
FIG. 2 is a side view of a probe head of the artificial airway sputum scab cleaner according to one embodiment of the present invention.

In an embodiment, one end of the sputum suction tube 4 away from the connection hub 1 is provided with a ball-shaped suction head 21.

Figure 3:
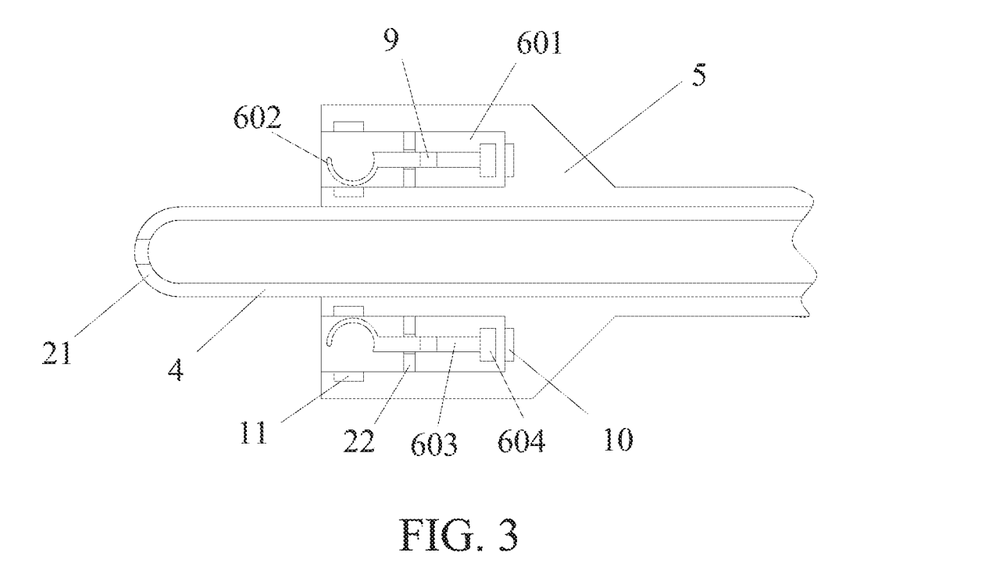
FIG. 3 is a cross-sectional view taken along A-A in FIG. 2.
Figure 4:
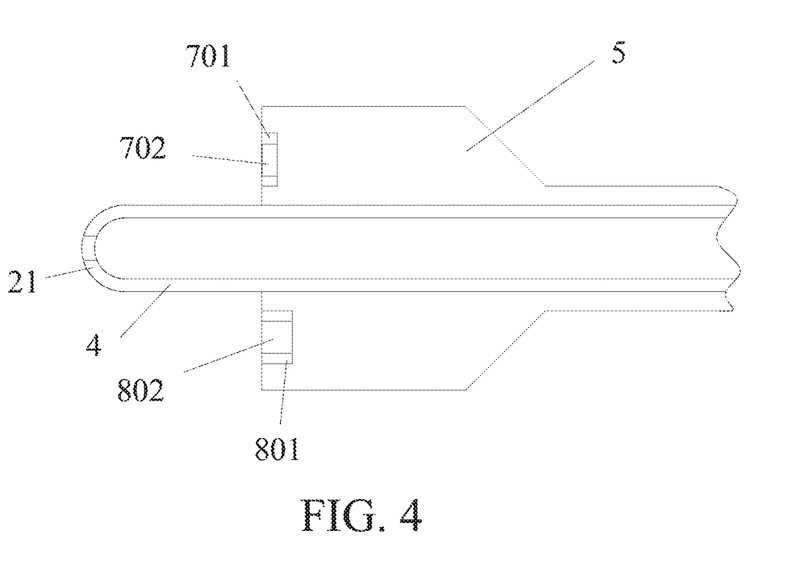
FIG. 4 is a cross-sectional view taken along B-B in FIG. 2.

In an embodiment, the hooking channel 601 is internally provided with a limiting circular plate 22.

In an embodiment, the number of the camera devices is 2 to 3.

In an embodiment, the number of the light beam devices is 2 to 3.

In an embodiment, the number of the hooking devices is 2 to 4.

In an embodiment, the connection hub is internally provided with a tube adapting interface and a video processor.

Figure 5:
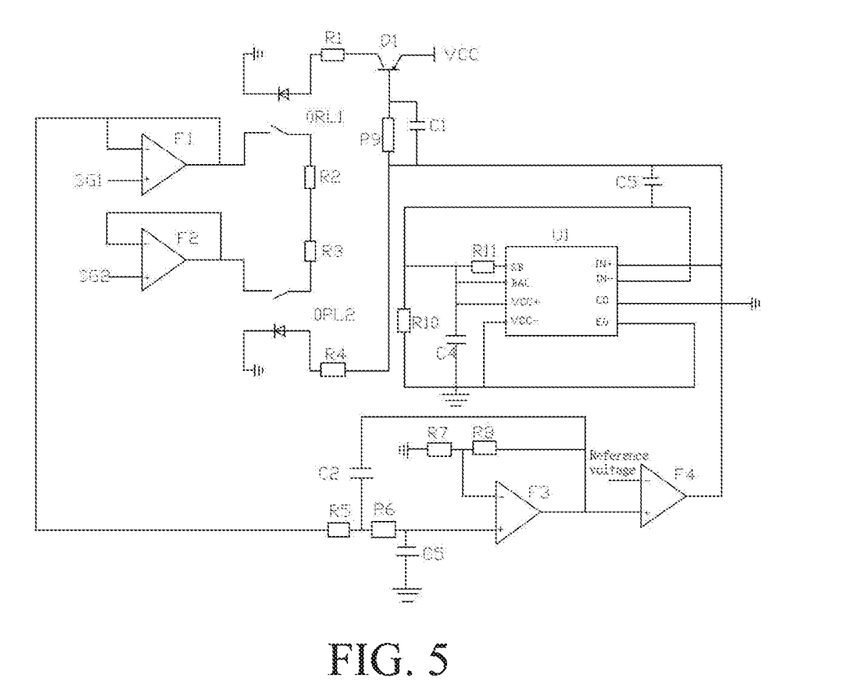
FIG. 5 is a schematic structural view of a signal conversion unit according to one embodiment of the present invention.

In one embodiment, as shown in FIG. 5, the connection hub further comprises a signal conversion unit which comprises a first operational amplifier, a second operational amplifier, a third operational amplifier, a fourth operational amplifier, a first resistor, a second resistor, a third resistor, a fourth resistor, a fifth resistor, a sixth resistor, a seventh resistor, an eighth resistor, a ninth resistor, a tenth resistor, an eleventh resistor, a first transistor, a first diode, a second diode, a first capacitor, a second capacitor, a third capacitor, a fourth capacitor, a fifth capacitor, a first power supply and a reference power supply, a comparator UI, a first light control relay, and a second light control relay.

As shown in FIG. 5, positive input terminals of the first operational amplifier and the second operational amplifier receive input signals respectively. Negative input terminals of the first operational amplifier and the second operational amplifier are respectively connected with respective output terminals. An input terminal of a relay in the first optical control relay is connected with an output terminal of the first operational amplifier. An input terminal of a relay in the second optical control relay is connected with an output terminal of the second operational amplifier. An output terminal of the relay in the first optical control relay is connected with one end of the second resistor. An output terminal of the relay in the second optical control relay is connected with one end of the third resistor. The other end of the second resistor is connected with the other end of the third resistor. A cathode of the first diode in the first light control relay is grounded. An anode of the first diode in the first light control relay is connected with one end of the first resistor. The other end of the first resistor is connected with a collector of the first transistor. An emitter of the first transistor is connected with the first power supply. A base of the first transistor is connected with one end of the ninth resistor and one end of the first capacitor respectively. The other end of the ninth resistor and the other end of the first capacitor are respectively connected with one end of the fourth resistor. The other end of the fourth resistor is connected with an anode of the second diode in the second light control relay. A cathode of the second diode in the second optical control relay is grounded. The output terminal of the first operational amplifier is also connected with one end of the fifth resistor. And the other end of the fifth resistor is connected with one end of the sixth resistor and one end of the second capacitor. The other end of the second capacitor is connected with the eighth resistor. A positive input terminal of the fourth operational amplifier and an output terminal of the third operational amplifier respectively. The other end of the eighth resistor is connected with the seventh resistor and a negative input terminal of the third operational amplifier respectively. The other end of the seventh resistor is grounded. A positive input terminal of the third operational amplifier is connected with the other end of the sixth resistor and one end of the third capacitor respectively. The other end of the third capacitor is grounded. A negative input terminal of the fourth operational amplifier is connected with the reference power supply. An output terminal of the fourth operational amplifier is connected with one end of the fifth capacitor, one end of the first capacitor, the other end of the ninth resistor and one end of the fourth resistor, respectively.

The comparator UI includes a pin SB, a pin BAL, a pin VCC+, a pin VCC−, a pin IN+, a pin IN−, a pin CO and a pin EO. The pin SB connected with one end of the eleventh resistor, and the other end of the eleventh resistor is connected with the pin BAL, the pin VCC+, one end of the fourth capacitor, one end of the tenth resistor, the other end of the fifth capacitor and the pin IN−. The other end of the tenth resistor is connected with the pin VCC− and the pin EO. The other end of the fourth capacitor and the pin CO are grounded. The pin IN+ is connected with one end of the fifth capacitor and the output terminal of the fourth operational amplifier.

In some embodiments, the first transistor is a PNP transistor.

The first power supply is 5.0 V. The first resistor has a resistance value of 330 ohms, the second resistor has a resistance value of 4.7 kiloohms, the third resistor has a resistance value of 10 kiloohms, and the fourth resistor has a resistance value of 330 ohms. The reference voltage is 2.5 V.

Both the first diode and the second diode use an IN4148 type diode.

The additional provision of the signal conversion unit can prevent interferences between other circuit devices in the signal conversion unit and an external working circuit and avoid using analog switches as signal switching elements, thus greatly reducing the on-resistance to a milliohm level. Moreover, the signal switching circuit of the present invention has the advantages of high signal switching speed, long service life, stable signal conversion, capability of effectively removing burrs, and capability of increasing the input signal range, thus realizing a conversion circuit with small resistance, high efficiency, stability and small interference, so as to improve the overall signal conversion quality, reduce the response time of electronic medical instruments, and thus improve the efficiency.

To sum up, with the above technical solution of the present invention, by inserting the probe head 5 into the patient, the power supply 12 powers the control button 13 to make the light beam device 7 and the camera device 8 cooperate. The internal condition of the artificial airway within the patient is presented on the display window 2 by the camera head 802, and an inspector operates according to the condition observed. In case of presence of sputum scab, the sputum scab is sucked into the sputum collecting tank 20 through the sputum suction device. If there is residue attached to the wall of the airway, the control button 13 can be used to energize the first coil 10 to generate magnetism and eject the hooking spoon 602, and then the direction of the hooking spoon 602 is adjusted through the attraction of the second coils 11 to the iron sheets 9. By constantly changing the direction of energization of the first coil 10, the hooking spoon 602 slides back and forth to facilitate the removal of foreign matters adsorbed on the wall of the airway, which is conducive to further removal of the sputum scab. The whole process is simple to operate with real-time monitoring, and is accurate, fast and safe to clean foreign matters, thus greatly saving the treatment time, saving the work intensity of doctors, and greatly reducing the pains of patients during treatment.

The above embodiments are merely preferred embodiments of the present invention, and are not intended to limit it. Any modifications, equivalent substitutions and improvements etc. made within the spirit and principles of the present invention should be included in the protection scope of the present invention.

What is claimed is:

1. An artificial airway sputum scab cleaner comprising: a connection hub (1);
   wherein a display window (2) is arranged in a side face of the connection hub (1);
   a detection tube (3) is arranged on a side face of the connection hub (1) opposite to the display window (2);
   a sputum suction tube (4) is inserted through the detection tube (3);
   a sputum suction device is arranged on a bottom face of the connection hub (1);
   a probe head (5) is arranged at one end of the detection tube (3) away from the connection hub (1);
   a hooking device (6), a light beam device (7) and a camera device (8) are arranged around a periphery of the sputum suction tube (4) on an end face of the probe head;
   the hooking device (6) comprises a hooking channel (601), a hooking spoon (602), a push rod (603) and a permanent magnet (604);
   the hooking channel (601) is arranged inside the probe head (5);
   the hooking spoon (602), the push rod (603) and the permanent magnet (604) are respectively arranged inside the hooking channel (601);
   the hooking spoon (602) is connected with the push rod (603) and the push rod (603) is connected with the permanent magnet (604);
   an iron sheet (9) is arranged on a side face of the push rod (603);
   a first coil (10) is arranged at one end of the hooking channel (601) close to the permanent magnet (604);
   a plurality of second coils (11) are equidistantly arranged at a side face of one end of the hooking channel (601) away from the permanent magnet (604);
   the light beam device (7) comprises a light beam groove (701) and a light beam lamp (702);

the light beam groove (701) is positioned on a surface of the probe head (5), and the light beam lamp (702) is fixed in the light beam groove (701);

the camera device (8) comprises a camera groove (801) and a camera (802);

the camera groove (801) is positioned on the surface of the probe head (5);

the camera (802) is fixed in the camera groove (801);

a power supply (12) and a control button (13) are provided on a top face of the connection hub (1);

the first coil (10), the second coils (11), the light beam lamp (702) and the camera (802) are respectively connected with the control button (13) through the connection hub (1);

the control button (13) is connected with the power supply (12);

the camera (802) is connected with the display window (2) through the connection hub (1);

the sputum suction device comprises a suction tube (14), a lateral valve cylinder (15), a longitudinal valve cylinder (16), a pull rod cylinder (17), a handle (18) and a pull rod (19);

one end of the suction tube (14) is connected with one end of the sputum suction tube (4) through the connection hub (1), and the other end of the sputum suction tube (4) is connected with the lateral valve cylinder (15);

the pull rod cylinder (17) is connected with the lateral valve cylinder (15);

the handle (18) is fixed on the pull rod cylinder (17);

the pull rod (19) is positioned inside the handle (18) and connected with the pull rod cylinder (17) by passing through the handle (18);

the longitudinal valve cylinder (16) is fixed to a bottom of a side face of the lateral valve cylinder (15); and a sputum collecting tank (20) is provided at a bottom end of the longitudinal valve cylinder (16).

2. The artificial airway sputum scab cleaner according to claim 1, wherein a ball-shaped suction head (21) is provided at one end of the sputum suction tube (4) away from the connection hub (1).

3. The artificial airway sputum scab cleaner according to claim 1, wherein a limiting circular plate (22) is provided inside the hooking channel (601).

4. The artificial airway sputum scab cleaner according to claim 1, wherein a number of the camera device (8) is 2 to 3, and a number of the light beam device (7) is 2 to 3.

5. The artificial airway sputum scab cleaner according to claim 1, wherein a number of the hooking device (6) is 2 to 4.

6. The artificial airway sputum scab cleaner according to claim 1, wherein the connection hub (1) further comprises a signal conversion unit, wherein the signal conversion unit comprises a first operational amplifier, a second operational amplifier, a third operational amplifier, a fourth operational amplifier, a first resistor, a second resistor, a third resistor, a fourth resistor, a fifth resistor, a sixth resistor, a seventh resistor, an eighth resistor, a ninth resistor, a tenth resistor, an eleventh resistor, a first transistor, a first diode, a second diode, a first capacitor, a second capacitor, a third capacitor, a fourth capacitor, a fifth capacitor, a first power supply and a reference power supply, a comparator UI, a first light control relay, and a second light control relay;

a positive input terminal of the first operational amplifier and a positive input terminal of the second operational amplifier receive input signals respectively;

a negative input terminal of the first operational amplifier and a negative input terminal of the second operational amplifier are respectively connected with an output terminal of the first operational amplifier and an output terminal of the second operational amplifier;

an input terminal of the first optical control relay is connected with an output terminal of the first operational amplifier;

an input terminal of the second optical control relay is connected with an output terminal of the second operational amplifier;

an output terminal of the first optical control relay is connected with one end of the second resistor;

an output terminal of the second optical control relay is connected with one end of the third resistor;

the other end of the second resistor is connected with the other end of the third resistor;

a cathode of the first diode in the first light control relay is grounded;

an anode of the first diode in the first light control relay is connected with one end of the first resistor;

the other end of the first resistor is connected with a collector of the first transistor;

an emitter of the first transistor is connected with the first power supply;

a base of the first transistor is connected with one end of the ninth resistor and one end of the first capacitor respectively;

the other end of the ninth resistor and the other end of the first capacitor are respectively connected with one end of the fourth resistor;

the other end of the fourth resistor is connected with an anode of the second diode in the second light control relay;

a cathode of the second diode in the second optical control relay is grounded;

the output terminal of the first operational amplifier is further connected with one end of the fifth resistor;

the other end of the fifth resistor is connected with one end of the sixth resistor and one end of the second capacitor;

the other end of the second capacitor is connected with the eighth resistor, a positive input terminal of the fourth operational amplifier and an output terminal of the third operational amplifier respectively;

the other end of the eighth resistor is connected with the seventh resistor and a negative input terminal of the third operational amplifier respectively;

the other end of the seventh resistor is grounded;

a positive input terminal of the third operational amplifier is connected with the other end of the sixth resistor and one end of the third capacitor respectively;

the other end of the third capacitor is grounded;

a negative input terminal of the fourth operational amplifier is connected with the reference power supply;

and an output terminal of the fourth operational amplifier is connected with one end of the fifth capacitor;

one end of the first capacitor, the other end of the ninth resistor and one end of the fourth resistor, respectively;

the comparator UI comprises a pin SB, a pin BAL, a pin VCC+, a pin VCC−, a pin IN+, a pin IN−, a pin CO and a pin EO;

wherein the pin SB is connected with one end of the eleventh resistor;

the other end of the eleventh resistor is connected with the pin BAL, the pin VCC+, one end of the fourth capacitor, one end of the tenth resistor, the other end of the fifth capacitor and the pin IN−;

the other end of the tenth resistor is connected with the pin VCC− and the pin EO;

the other end of the fourth capacitor and the pin CO are grounded; and the pin IN+ is connected with one end of the fifth capacitor and the output terminal of the fourth operational amplifier.

7. The artificial airway sputum scab cleaner according to claim 6, wherein the first transistor is a PNP transistor.

8. The artificial airway sputum scab cleaner according to claim 6, wherein the first power supply is 5.0 V;

the first resistor has a resistance value of 330 ohms;

the second resistor has a resistance value of 4.7 kiloohms;

the third resistor has a resistance value of 10 kiloohms;

the fourth resistor has a resistance value of 330 ohms; and the reference voltage is 2.5 V.

9. The artificial airway sputum scab cleaner according to claim 6, wherein both the first diode and the second diode are IN4148 type diode.

* * * * *